United States Patent
Delaey et al.

(12)

(10) Patent No.: US 6,204,359 B1
(45) Date of Patent: Mar. 20, 2001

(54) FORM OF AMPHIREGULIN, METHODS FOR PRODUCING AND USING THE SAME AND COMPOSITIONS COMPRISING THE SAME

(75) Inventors: Bernard Delaey, Zingem; Jos Raymackers, Nazareth; Hugo Van Heuverswyn, Laarne, all of (BE)

(73) Assignee: Innogenetics N.V. (BE)

( * ) Notice: Subject to any disclaimer, the term of this patent is extended or adjusted under 35 U.S.C. 154(b) by 0 days.

(21) Appl. No.: 09/077,977

(22) PCT Filed: Dec. 23, 1996

(86) PCT No.: PCT/EP96/05831

§ 371 Date: Jun. 10, 1998

§ 102(e) Date: Jun. 10, 1998

(87) PCT Pub. No.: WO97/23507

PCT Pub. Date: Jul. 3, 1997

(30) Foreign Application Priority Data

Dec. 22, 1995 (EP) .................................................. 95870138

(51) Int. Cl.[7] .......................... C07K 14/475; C07K 9/00; A61K 38/00; A61K 38/17; A61K 38/14

(52) U.S. Cl. .......................... 530/322; 530/324; 530/397; 530/412; 530/413; 530/416; 514/8; 514/12

(58) Field of Search ..................................... 530/322, 324, 530/397, 412, 413, 416; 514/8, 12

(56) References Cited

PUBLICATIONS

Cunningham et al, Science vol. 244, pp. 1081–1085, Jun. 1989.*

George et al, Macromolecular sequencing and synthesis, edited by Schlesinger, Alan R. Liss, Inc, New York, Chapter 12, pp. 127–149, 1988.*

Zhang et al, "An . . . Cellular Proteins", Proc. Natl. Acad. Sci. USA, vol. 90, 1993, pp. 2217–2221, XP000575966.

Adam et al, "Modulation . . . Terminal Tail", Biochem. Biophys. ACTA vol. 1266, 1955, pp. 83–90, XP000574486.

* cited by examiner

Primary Examiner—Prema Mertz
Assistant Examiner—Fozia Hamud
(74) Attorney, Agent, or Firm—Bierman, Muserlian and Lucas

(57) ABSTRACT

An isolated and purified polypeptide having heparin binding properties with the amino acid sequence of SQ ID No: 1 and pharmaceutical compositions for treating skin wounds.

14 Claims, 6 Drawing Sheets

FORM OF AMPHIREGULIN, METHODS FOR PRODUCING AND USING THE SAME AND COMPOSITIONS COMPRISING THE SAME

This application is a 371 of PCT/EP96/05831 filed on Dec. 23, 1996.

The present invention relates to the field of wound healing factors. More particularly, the present invention relates to a novel form of amphiregulin produced by keratinocytes, as well as analogs thereof, methods for their production, their uses, more particularly the use thereof in treatment of a variety of conditions including wound healing, skin disorders and cancer.

BACKGROUND OF THE INVENTION

After wounding of the skin, one of the objectives is to close the defect as quickly as possible. This is especially important in the case of extensive burns, in order to limit infection risk and fluid loss. Apart from several dressing and grafting techniques developed over the past decades, the use of cultured epidermal sheets has gained increasing attention. This technology allows the covering of the wound with a stratified sheet of living keratinocytes, derived either from the patients' own skin (autologous sheets) or from other donors (allogeneic sheets). Interestingly, although it has been shown that allogeneic keratinocyte sheets have only a limited survival time on the acceptor wound, they have the same clinical effect as autologous sheets when used in combination with split thickness meshed autografts or when applied on partial thickness wounds. This has been explained by hypothesising the existence of wound healing factors produced by these keratinocytes. These factors enhance the wound repair process by stimulating the proliferation and/or migration of the various cell types present in the wound. A new autologous epidermis can thus be formed by the outgrowth from keratinocytes present in the meshed skin autografts or epidermal appendages (e.g. sweat glands, hair follicles).

Although clinically successful in many cases, and sometimes lifesaving, cultured keratinocyte sheets suffer from a number of obvious disadvantages. They are extremely expensive, time-consuming to prepare and difficult to transport, apply and preserve for prolonged periods. Therefore, it would be desirable to develop a wound therapeutic based directly on keratinocyte-derived wound repair factors, without the need of using the living cells themselves.

Several growth factors with potential therapeutic interest in the field of wound healing have been identified or isolated already in keratinocytes. These include, among others, TGF-α, bFGF, amphiregulin and HB-EGF. However, to date, none of these factors has proven to provide the same clinical potential as the living keratinocyte cultures.

One factor of particular interest is amphiregulin (AR). This is a heparin-binding glycoprotein of approximately 20 kDa which was originally purified from phorbol ester-treated MCF-7 human breast carcinoma cells. The factor belongs to the EGF-family of growth factors and stimulates the proliferation of several cell types (including keratinocytes and some fibroblast cell lines), while inhibiting the proliferation of other cells (including many carcinoma cell lines) (Shoyab et al., Proc. Natl. Acad. Sci. USA 85, 6528–6532 (1988); Shoyab et al., Science 243, 1074–1076 (1989)). Sequencing of AR revealed the existence of two forms, containing 78 and 84 amino acids, respectively (Shoyab et al, Science 243, 1074–1076 (1989), Plowman et al., Mol. Cell. Biol. 10, 1969–1981 (1990)). The N-termini of these two subforms were reported to be located at residues 101 and 107 of the preprotein sequence (taking the initiation methionine as residue No.1), whereas the C-terminus was reported to be located at residue 184 of the preprotein sequence. Later studies revealed however that the C-terminal processing site is located probably at least 2 amino acid residues downstream from the originally reported one (Adams et al., Biochim. Biophys. Acta 1266, 83–90 (1994); Thompson et al., J. Biol. Chem. 271, 17927–17931 (1996)). This means that the total length of the published amphiregulin subforms should be at least 80 and 86 amino acids, respectively. To avoid confusion, we will henceforth designate the subforms with their respective N-terminal- and C-terminal endpoints (taking the initiation methionine of the preprotein as residue No. 1). Glycosylation seems not to be important for biological activity of the molecule (Shoyab et al., Proc. Natl. Acad. Sci. USA 85, 6528–6532 (1988)). Later studies revealed that a major keratinocyte autocrine factor is also amphiregulin (Cook et al., Mol. Cell. Biol., 11, 2547–2557 (1991); Cook et al., In Vitro Cell. Dev. Biol. 28A, 218–222 (1992); Piepkorn et al., J. Cell. Physiol. 159, 114–120 (1994)). In cultured keratinocyte conditioned media also, two subforms starting at residues 101 and 107 of the preprotein were detected. A special feature of AR is that its biological activity is completely blocked in the presence of heparin sulphate. It has been reported to be the only growth factor displaying this property (Cook et al., Mol. Cell. Biol., 11, 2547–2557 (1991); Cook et al., In Vitro Cell. Dev. Biol. 28A, 218–222 (1992), Piepkorn et al., J. Cell. Physiol. 159, 114–120 (1994)). The isolation, properties, cloning and potential therapeutical use of AR are disclosed in U.S. Pat. No. 5,115,096 (May 19, 1992), assigned to Oncogen (Seattle).

AIMS OF THE INVENTION

It is an aim of the present invention to isolate and characterize a novel form of amphiregulin.

It is also an aim of the present invention to provide analogs of this novel form of amphiregulin.

It is also an aim of the present invention to provide a composition comprising said novel form of amphiregulin or its analogs.

It is also an aim of the present invention to provide methods for producing said novel form of amphiregulin.

It is further an aim of the present invention to provide pharmaceutical compositions comprising as an active ingredient the novel form of amphiregulin of the present invention.

It is further an aim of the present invention to provide methods of treating diseases comprising the use of said novel form of amphiregulin.

All the aims of the present invention have been met by the following embodiments as set out below.

SUMMARY OF THE INVENTION

The present invention relates to the discovery of a new form of amphiregulin, referred to as AR97-187. The new form differs from the hitherto described amphiregulin forms in that it contains 4 additional amino acids at its N-terminal end. It also differs from already described forms with respect to its interaction with heparin in that its biological activity is only marginally reduced in the presence of heparin. Possibly, AR97-187 is produced by differentiating keratinocytes. AR97-187 is of therapeutical interest for the treatment of a variety of conditions, including wound healing, skin disorders and cancer.

DETAILED DESCRIPTION OF THE INVENTION

The present invention relates more particularly to a polypeptide representing a novel form of amphiregulin referred to as AR97–187 (or AR88) and characterized by the novel N-terminal amino amino sequence extension: NH$_2$-IVDD (SEQ ID NO 14).

As is described in detail in the examples section, a novel form of amphiregulin most probably containing at least 90 amino acids, and with the N-terminal end starting at residue 97 of the preprotein sequence, was identified by the present inventors. In the prior art, two other forms (starting respectively at residues 101 and 107 of the preprotein sequence) have been isolated. The novel form is produced by stratified keratinocyte cultures, cultured in a high calcium, serum-containing medium. These cultures are substantially different from those used in the prior art, particularly with respect to the differentiation state of the cells, and to the fact that they form multilayered, stratified sheets. Possibly, these differences constitute one reason why these cultures produce the presently identified novel form of amphiregulin.

The term "stratified" refers to sheets of keratinocytes comprising at least two cell layers, preferably at least three cell layers, more preferably at least 4 cell layers.

The medium which is used to obtain said stratified keratinocyte cultures essentially contains the following components: DMEM/Ham's F12 (3/1), 10% fetal calf serum, 12 ng/ml natural mouse EGF, 0.4 µg/ml hydrocrotisone, 11 ng/ml cholera toxin, 4.9 µg/ml transferrin, 6 µg/ml insulin, 1.4 ng/ml trioodothyronin and 0.13 mM adenin.

The present invention thus also relates to a novel form of amphiregulin obtainable from multilayered, stratified keratinocyte cultures which are cultured in a high calcium, serum-containing medium.

The complete sequence of this novel form of AR97-187 amphiregulin is preferably as follows:

5 or 11 of SEQ ID NO 1 (corresponding to residues 101 or 107 of the preprotein sequence) are for instance described in U.S. Pat. No. 5,115,096, in Shoyab et al., Science 243, 1074–1076 (1989), Plowman et al., Mol, Cell. Biol. 10, 1969–1981 (1990), and in Cook et al., Mol. Cell. Biol. 11, 2547–2557 (1991).

The new form of amphiregulin of the present invention is shown to have the following surprising properties:

- it elutes from a heparin affinity column at a NaCl concentration between approximately 500 and 1000 mM, preferably between approximately 550 and 900 mM more preferably between 600 and 750 mM. This is in contrast to the non-differentiated keratinocyte-derived amphiregulin preparations in the prior art, which were described to elute at approximately 1.75 M (Cook et al., Mol. Cell. Biol. 11, p.2547–2557 (1991)).
- its mitogenic activity is not completely abolished in the presence of heparin, under conditions where the activity of a MCF-7-derived amphiregulin preparation (which contains only the 78 and 84 amino acid forms of amphiregulin) was nearly completely inhibited. Prior art data indicate that the activity of both MCF-7-derived and non-differentiated keratinocyte-derived amphiregulin is nearly completely blocked by heparin sulphate.
- it has a mitogenic activity for Balb 3T3 cells, whereas the other forms of amphiregulin were reported to be non-active on these cells (Shoyab et al., Proc. Natl. Acad. Sci U.S.A 85, 6528–6532 (1988); U.S. Pat. No. 5,115, 096)
- it stimulates colony formation of NRK cells in a soft agar colony formation assay at low seeding density, in contrast to the other forms of amphiregulin (Shoyab et al., Science 243, 1074–1076 1989)).

The expression "not completely inhibited by heparin" is to be understood as meaning that the mitogenic activity, as measured in the Balb/MK bioassay described in example 3, is inhibited by no more than about 80%, preferably by no more than about 50%, even more preferably by no more than about 30% in the presence of 10 µ/ml of heparin. This

```
            5         10        15        20        25        30    (SEQ ID NO 1)
            |         |         |         |         |         |
 1                                                              I V D D S V R
                                                                V E Q V V K P
                                                                P Q N K T E S
                                                                E N T S D K P
                                                                            K R
31                                                              K K K G G K N
                                                                G K N R R N R
                                                                K K K N P C N
                                                                A E F Q N F C
                                                                            I H
61                                                              G E C K Y I E
                                                                H L E A V T C
                                                                K C Q Q E Y F
                                                                G E R C G E K
                                                                            S M
                                                                            K
```

According to another embodiment, the present invention also relates to novel amphiregulin forms which differ from SEQ ID NO 1 in that their C-terminus is longer or shorter than the C-terminus of SEQ ID NO 1.

The expression "a novel form of amphiregulin" is to be interpretated as amphiregulin comprising 4 additional amino acids IVDD (SEQ ID NO 14) at its amino terminus. This novel form of amphiregulin preferably has a total of at least 90 amino acids. Amphiregulin isoforms starting at residues implies also that said AR97-187 polypeptide or its analogs have retained more than about 20%, preferably more than about 50%, even more preferably more than about 70% of its activity in the presence of heparin. In determining these heparin inhibition percentages, it has to be understood that the concentration of AR97-187 or the other amphiregulin isoforms in the Balb/MK bioassay should be between 0.25 and 3 units/ml, preferably between 0.5 and 2.5 U/ml, even more preferably between 1 and 2 U/ml (with one unit defined as the amount of mitogenic activity giving rise to the same amount of incorporated label as obtained with 1 ng/ml of natural mouse EGF).

The expression "nearly completely inhibited by heparin" is to be understood as meaning that the mitocenic activity, as is measured in the Balb/MK bioassay described in example 3, is inhibited by at least 85%, preferably by at least 90%, more preferably by at least 95%, even more preferably by at least 98% in the presence of 10 µg/ml of heparin. This implies also that said AR97-187 polypeptide or its analogs have retained no more than about 15%, preferably no more than about 10%, more preferably no more than about 5%, even more preferably no more than about 2% of its activity in the presence of heparin. In determining these heparin inhibition percentages, it has to be understood that the concentration of AR97-187 or the other amphiregulin isoforms in the Balb/MK bioassay should be between 0.25 and 3 units/ml, preferably between 0.5 and 2.5 U/ml, even more preferably between 1 and 2 U/ml (with one unit defined as the amount of mitogenic activity giving rise to the same amount of incoporated label as obtained with 1 ng/ml of natural mouse EGF). An example of such an inhibition experiment is provided in example 6 and FIG. 4. This example shows that in the absence of heparin the AR97-187 preparation, at a dilution of 1/150, produces an activity of 1.56 U/ml, which is similar to the activity obtained with MCF-7 AR (a heparin-purified amphiregulin preparation from MCF-7 cells, containing the isoforms starting at residues 101 and 107 of the preprotein sequence) at a dilution of 1/1600, namely 1.25 U/ml. Nevertheless, when tested at the same concentration in the presence of 10 µg/ml of heparin, the AR97-187 preparation has a residual activity of 0.52 U/ml (i.e. 33% of the activity in absence of heparin), whereas the MCF-7 AR preparation has a residual activity of only 0.01 U/ml (i.e. 0.8% of the activity in absence of heparin). This shows that, according to the abovementioned definitions, the AR97-187 preparation is not completely inhibited by heparin, while the other amphiregulin isoforms are nearly completely inhibited.

The present invention further relates to a composition comprising AR97–187 amphiregulin as defined above. Said composition can be a polypeptide composition and can contain, apart from AR97-187, any other polypeptide or any other component or excipient known in the art.

According to a preferred embodiment, the present invention relates to a polypeptide preparation which contains approximately equal amounts of the amphiregulin isoform starting at residue 97 of the preprotein sequence and of the amphiregulin isoform starring at residue 107 of the preprotein sequence.

According to another embodiment, the present invention relates also to any analog of the AR97-187 amphiregulin in which deletions, insertions and/or substitutions (conservative or non-conservative) have been made in such a way that these 4 additional N-terminal amino acids are unchanged and that the activity of said amphiregulin is largely retained.

Said analogs differ preferably in less than 25%, more preferably in less than 20%, most preferably in less than 10% of their amino acids from AR97-187 of the present invention.

The term "analog" as used throughout the specification or claims to describe the proteins or peptides of the present invention, includes any protein or peptide having an amino acid residue sequence substantially identical to a sequence specifically shown herein in which one or more residues have been conservatively substituted with a biologically equivalent residue. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that the resulting protein or peptide is biologically equivalent to the protein or peptide of the invention.

"Chemical derivative" refers to a protein or peptide having one or more residues chemically derivatized by reaction of a functional side group. Examples of such derivatized molecules, include but are not limited to, those molecules in which free amino groups have been derivatized to form amine hydrochlorides, p-toluene sulfonyl groups, carbobenzoxy groups, t-butyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The proteins or peptides of the present invention also include any protein or peptide having one or more additions and/or deletions or residues relative to the sequence of a peptide whose sequence is shown herein, so long as the peptide is biologizally equivalent to the proteins or peptides of the invention.

The term "biologically equivalent" refers to the activity of said polypeptide or peptide which is largely retained as explained above.

Said activity of said amphiregulin involves particularly a mitogenic activity which is partially inhibited by heparin as is detailed below.

Alternatively, the present invention also relates to analogs having largely retained any other activity of the AR97-187.

The activity of the AR97-187 polypeptide and its analogs may be assayed by any method known in the art which measures an activity known to exist for amphiregulins, for instance as described in U.S. Pat. No. 5,115,096, Cook et al., Mol. Cell. Biol. 11, p.2547–2557 (1991), Shoyab et al., Science 243, p.1074–1076 (1989) and Shoyab et al., Mol. Cell. Biol. 10, p.1969–1981 (1990), the contents of which are hereby incorporated by reference.

The polypeptides or peptides of the invention are regarded as being strongly mitogenic if they show an ED50 of less than 10 ng/ml, preferably less than 5 ng/ml, more preferably less than 1 ng/ml; ED50 being defined as the concentration needed to obtain half-maximal stimulation of the cells. In addition, maximal stimulation values obtained with AR97-187 in the above mentioned assay should be at least 10%, preferably at least 25%, more preferably at least 50% of the values obtained with a maximally stimulating dose of EGF.

Also comprised in the present invention are peptides comprising deletions of one or several amino acids of AR97-187 or its analogs, more particularly C-terminal deletions of AR97-187 (f.i. as represented in SEQ ID NO 1) in such a way that peptides of varying length can be obtained. Said deletion peptides can for instance consist of less than 60 (amino acid 1 to 60 or less of SEQ ID NO 1), less than 50 (amino acid 1 to 50 or less of SEQ ID NO 1), less than 40 (amino acid 1 to 40 or less of SEQ ID NO 1), less than 30 (amino acid 1 to 30 or less of SEQ ID NO 1), or less than 20 amino acids (amino acid 1 to 20 or less of SEQ ID NO 1) in length, as long as said peptides contain the IVDD (SEQ ID NO 14) N-terminal sequence.

Also comprised within the present invention are polypeptides, particularly recombinant ones, which comprise in their amino acid sequence at least one of the afore-mentioned C-terminally deleted peptides of said AR97-187 polypeptide or its analogs.

Also comprised within the present invention are fusion peptides of AR97-187 or its analogs.

The term 'fusion polypeptide' intends a polypeptide in which the AR97-187 polypeptide or its analogs are part of a single continuous chain of amino acids, which chain does not occur in nature. The fusion polypeptides may also contain amino acid sequences exogenous to amphiregulin (heterologous sequences).

The terms polypeptide and peptide are used interchangeably in the remainder of the present invention.

Said AR97-187 polypeptide or its analogs may further be modified by any type of modification known in the art of polpeptide chemistry at either the N or the C terminus of the amino acid chain. Also included are polypeptides containing one or more analogues of an amino acid (including for instance unnatural amino acids, PNA, etc.), polypeptides with substituted linkages, as well as other modifications known in the art, both naturally occurring and non-naturally occurring. The AR97-187 polypeptide or its analogs may also include post-expression modifications such as glycosylations, acetylations, phosphorylations and the like.

According to a further embodiment, the present invention relates to an AR97-187 polypeptide which is characterized as being produced by and isolated from keratinocytes.

Said keratinocytes are preferably human keratinocytes, cultured in a medium allowing the formation of partially differentiated, multilayered epithelial sheets. More preferably said keratinocytes are cultured in a high calcium, serum-containing medium as illustrated in the Examples section. It may further be anticipated that non-human keratinocytes or other cells could produce versions of amphiregulin which are still active, and that the production step of in vitro growth of those cells could be replaced by direct retrieval from corpses.

According to a further embodiment, the present invention relates to an AR97-187 polypeptide obtainable by a purification process comprising:

(a) preparation of a 24-hour-conditioned culture medium from a multilayered keratinocyte culture, (b) applying the culture medium obtained in step (a) on a hydroxyapatite affinity column and eluting the column with approximately 200 mM NaCl, (c) applying the hydroxyapatite eluate obtained in step (b) onto a heparin affinity column and collecting the bioactive fractions eluting between approximately 500 and 1000 mM NaCl, preferably between 550 and 900 mM, more preferably between 600 and 750 mM.

(d) applying the heparin eluate obtained in step (c) onto a Poros HS cation exchange column, eluting the column with a NaCl gradient at approximately pH 7.2 and collecting the bioactive fractions eluting between approximately 500 and 1200 mM NaCl, more preferably between approximately 550 and 1000 mM, even more preferably between approximately 650 and 900 nM.

(e) applying the Poros HS eluate obtained in step (d) onto a HEMA CM cation exchange column, eluting the column with a pH gradient at approximately pH 7.2 and collecting the bioactive fractions eluting between approximately 0.1 and 0.7 M NaCl, preferably between approximately 0.15 and 0.6 M, more preferably between approximately 0.2 and 0.4 M, (f) applying the HEMA CM eluate obtained in step (e) onto a Zorbax C8 microbore RPC column, eluting the column with an acetonitrile gradient in 0.1% trifluoroacetic acid and collecting the bioactive fractions eluting between approximately 16 and 32% acetonitrile, preferably between approximately 18 and 30%, more preferably between approximately 21 and 27%.

The different columns or chromatography matrices referred to are for instance supplied by the following manufacturers Hydroxyapaptite is from Bio-Rad Laboratories, Ltd. (Hercules, Calif., USA); Poros Heparin and Poros HS are from Perseptive Biosystems (Cambridge, Mass., USA); the Hema CM column is from Alltech Associates, Inc. (Deerfield, Ill., USA) and the Zorbax C8 column is from LC Packings (Amsterdam, The Netherlands) and are used according to the manufacturers instructions.

During the purification process, bioactivity may be measured in a Balb/MK bioassay as described in example 3.

An important aspect of the purification procedure is that the starting material is a conditioned culture medium from stratified multilayered keratinocyte cultures, in contrast to the medium used by Cook et al. (Mol. Cell. Biol. 11, p.2547–2557 (1991)), which was derived from non-differentiated keratinocyte cultures. Differentiated keratinocytes may differ from non-differentiated keratinocytes by the possibility to produce the presently disclosed novel AR97-187 form of amphiregulin.

According to a further embodiment, the present invention relates to a recombinantly expressed AR97-187 polypeptide or an analog thereof as defined above.

The term "recombinantly expressed" refers to the fact that the proteins of the present invention are produced by a recombinant expression method be it in prokaryotes, lower eukaryotes or higher eukaryotes.

The term 'lower eukaryote' refers to host cells such as yeast, fungi and the like. Lower eukaryotes are generally (but not necessarily) unicellular. Preferred lower eukaryotes are yeasts, particularly species within Saccharomyces, Schizosaccharomyces, Kluyyeromyces, Pichia (e.g. *Pichia pastoris*), Hansenula (e.g. *Hansenula polymorpha*), Yarowia, Schwaniomyces, Schizosaccharomyces, Zygosaccharomyces and the like. *Saccharomyces cerevisiae, S. carlsbergensis* and *K. lactis* are the most commonly used yeast hosts, and are convenient fungal hosts.

The term 'prokaryotes' refers to hosts such as *E coli,* Lactobacillus, Lactococcus, Salmonella, Streptococcus, *Bacillus subtilis* or Streptomyces. Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The present invention thus also relates to a recombinant polynucleotide or a recombinant nucleic acid encoding said AR97-187 or its analogs as defined above.

The term 'recombinant polynucleotide or recombinant nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The present invention further relates to a recombinant vector comprising said recombinant polynucleotide or nucleic acid under the control of an appropriate regulatory sequence.

The present invention further relates to a recombinant host cell transformed with a recombinant vector carrying a nucleic acid encoding said AR97-187, or its analogs.

The term 'vector' is a replicon further comprising sequences providing replication and/or expression of a desired open reading frame.

The term 'replicon' is any genetic element, e.g., a plasmid, a chromosome, a virus, a cosmid, etc., that behaves as an autonomous unit of polynucleotide replication within a cell: i.e., capable of replication under its own control.

A variety of vectors may be used to obtain recombinant expression of the AR97-187 polypeptides or its analogs. Lower eukaryotes such as yeasts and glycosylation mutant strains are typically transformed with plasmids, or are transformed with a recombinant virus. The vectors may replicate within the host independently, or may integrate into the host cell genome.

Higher eukaryotes may be transformed with vectors, or may be infected with a recombinant virus, for example a recombinant vaccinia virus. Techniques and vectors for the insertion of foreign DNA into vaccinia virus are well known in the art, and utilize, for example homologous recombination. A wide variety of viral promoter sequences, possibly terminator sequences and poly(A)-addition sequences, possibly enhancer sequences and possibly amplification sequences, all required for the mammalian expression, are available in the art.

Also known are insect expression transfer vectors derived from baculovirus Autographa californica nuclear polyhedrosis virus (AcNPV), which is a helper-independent viral expression vector. Expression vectors derived from this system usually use the strong viral polyhedrin gene promoter to drive the expression of heterologous genes. Different vectors as well as methods for the introduction of heterologous DNA into the desired site of baculovirus are available to the man skilled in the art for baculovirus expression. Also different signals for posttranslational modification recognized by insect cells are known in the art.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

An 'open reading frame' (ORF) is a region of a polynucleotide sequence which encodes a polypeptide and does not contain stop codons; this region may represent a portion of a coding sequence or a total coding sequence.

A 'coding sequence' is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to MRNA, DNA (including cDNA), and recombinant polynucleotide sequences. In case the coding sequence is formed by placing an initiation codon in front of the sequence IVDD (SEQ ID No. 1), the expression product will contain a methionine residue at its N-terminus (which will hence start with the sequence MIVDD).

The nucleic acid segment encoding AR97-187 or its desired analog inserted into the vector sequence may be attached to a signal sequence. Said signal sequence may be that from a non-amphiregulin source, e.g. the IgG or tissue plasminogen activator (tpa) leader sequence for expression in mammalian cells, or the α-mating factor sequence for expression into yeast cells, but particularly preferred constructs according to the present invention contain signal sequences appearing in the arnphiregulin cDNA before the respective start points of the AR97-187 protein.

Said recombinant host cells can be prokaryotes, or lower or higher eukaryotes as explained above.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

According to a further embodiment, the present invention relates to an AR97-187 polypeptide or an analog thereof (recombinant or not) which is glycosylated.

According to a further embodiment, the present invention relates to an AR97-187 polypeptide or an analog thereof (recombinant or not) which is not glycosylated.

The present invention further relates to a composition comprising an AR97-187 or its analogs as defined here above. More particularly, the present invention relates to a composition comprising a mixture of the AR97-187 form of amphiregulin or its variants as described above and an already known form of amphiregulin as described in the background art section.

Other preferred compositions according to the present invention comprise mixtures of an AR97-187 polypeptide or its variants of the present invention mixed with a growth regulating factor such as any factor belonging to the EGF family of growth factors, any of the fibroblast growth factors, any of the PDGF isoforms, any of the TGF-β isoforms or any of the insulin-like growth factors.

Said compositions contain at least a pharmaceutically active amount of AR97-187 of the invention or an analog thereof.

According to a further embodiment, the present invention relates to a composition or preparation comprising AR97-187 or one of its analogs, with said composition being strongly mitogenic for for instance Balb/MK keratinocytes, Balb 3T3 fibroblasts and Swiss albino 3T3 fibroblasts as assayed in for instance a tritium thymidine incorporation assay as described in example 6.

According to a further embodiment, the present invention relates to a composition comprising AR97-187 or its analogs further characterized in that their mitogenic activity as defined above is not completely inhibited by heparin (10 µAg/ml).

The present invention further relates to a method for producing the AR97-187 polypeptide or its analogs according to the present invention.

Said methods may include recombinantly expressing the polypeptides by culturing a suitable host as defined above, which is transformed with a recombinant vector as defined above, comprising:

growing a host cell as defined above transformed with a recombinant vector according to the present invention in a suitable culture medium, causing expression of said vector sequence as defined above under suitable conditions.

recovering said recombinant protein by for instance affinity purification, gelfiltration.

or any other suitable technique known in the art from the culture medium conditioned by the host cells or from a lysate of the host cells.

Alternatively the peptides or polypeptides of the present invention may be prepared by classical chemical synthesis. The synthesis may be carried out in homogenous solution or in solid phase. For instance, the synthesis technique in homogeneous solution which can be used is the one described by Houbenweyl ("Methoden der organischen chemie" (Method of organic chemistry) edited by Wunsh, vol. 15-I and II. Thieme, Stuttgart, 1974). The polypeptides or peptides of the invention can also be prepared in solid phase according to methods described for instance by Atherton and Shepard ("Solid phase peptide synthesis", IRL press, Oxford, 1989).

Another preferred method of preparing the AR97-187 polypeptides or its analogs of the present invention comprises:

growing human keratinocytes and allowing them to differentiate into multilayered sheets recovering AR97-187 polypeptide or its analogs by for instance affinity purification, gelfiltration, or any other suitable technique known in the art from the culture medium conditioned by the keratinocytes or from a lysate of the keratinocytes.

The present invention further relates to a medicament comprising as an active ingredient an AR97-187 polypeptide or an analog thereof in a pharrnaceutically acceptable recipient.

The present invention further relates to an AR97-187, polypeptide or its analogs for use as a medicament.

The present invention further relates to the use of an AR97-187 polypeptide or its analogs in a method for treatment of a variety of disease or injury conditions, more particularly for treatment of at least one of the following conditions: skin wounds (including burns, ulcers, surgical wounds etc.), corneal wounds, tympanic membrane reconstructions, intestinal or stomach ulcers, dermatological disorders bone disorders, cancer (including colon, prostate, ovarium, pancreas, etc.) or any other illness state where an amphiregulin would be required or useful.

The present invention relates also to a method of treatment of any of the above-given diseases comprising administering an effective amount of an AR97-187 polypeptide or one of its analogs.

The term "effective amount" refers to an amount of the AR97-187 polypeptide or its analogs sufficient to effect the desired treatment. This amount will vary according to the application and may vary depending on the species, age, general condition of the individual, the severity of the condition being treated, the particular polypeptide and its mode of administration. An appropriate effective amount can be readily determined only by using routine experimentation.

The polypeptides of the invention may be administrated in any physiologically acceptable form which is considered appropriate for the specific application. This includes formulation in an aqueous liquid, a gel, a creme or an ointment. For some purposes, it may be especially advantageous to administrate the polypeptides in the form of a controlled release formulation, so that the target tissues or organs are exposed to an appropriate dose for a prolonged time. There are numerous controlled release devices known to the man of the art. For instance, the peptides may be incorporated in microspheres from which they are gradually released through diffusion or through breakdown of the microsphere matrix. Another application form is by incorporation of the peptides in liposomes or similar lipid vesicles. For other applications, e.g. skin wounds, the peptides may be incorporated in medicated bandages or wound dressings. Particularly suitable materials for the fabrication of such microparticles or bandages include biodegradable materials such as polylactides, collagens, dextranomers, gelatins, alginates or other gelable polysaccharides, etc. The optimal application form will vary according to the specific condition to be treated, the desired release profile, the dose to be delivered, the intended shelf life of the composition, etc.

The present invention further relates to the use of an AR97-187 polypeptide or its analogs for the preparation of a medicament for treating any of the above-mentioned diseases.

The present invention further relates to antibodies specifically raised against an AR97-187 polypeptide or one of its analogs according to the present invention.

Said antibodies are preferably monoclonal antibodies and are preferably specifically reactive with the AR97-187 polypeptide or analogs thereof of the present invention.

The monoclonal antibodies of the invention can be produced by any hybridoma liable to be formed according to classical methods from splenic cells of an animal, particularly from a mouse or rat, immunized against the amphiregulin polypeptide or analogs thereof according to the invention as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains or from cDNA clones coding for H and L chains.

Alternatively the monoclonal antibodies according to this preferred embodiment of the invention may be human monoclonal antibodies. Such human monoclonal antibodies are prepared, for instance, by means of human peripheral blood lymphocytes (PBL) repopulation of severe combined immune deficiency (SCID) mice (for recent review, see Duchosal et al. 1992) or by screening Eppstein Barr-virus-transformed lymphocytes of infected or vaccinated individuals for the presence of reactive B-cells by means of the antigens of the present invention.

The invention also relates to the use of the proteins of the invention, analogs thereof, or peptides derived therefrom for the selection of recombinant antibodies by the process of repertoire cloning (Persson et al., 1991).

Certain pathological conditions may be the consequence of an over- or under-expression, or of the inappropriate expression of the presently described amphiregulin isoform, or of the expression of a defective variant of present isoform. Therefore, the present polypeptides, peptides, fragments of present peptides or antibodies directed towards them may also be useful for diagnostic purposes, to screen and monitor abovementioned disease states.

EXAMPLES

1. Keratinocyte Culturing

Figure 1:
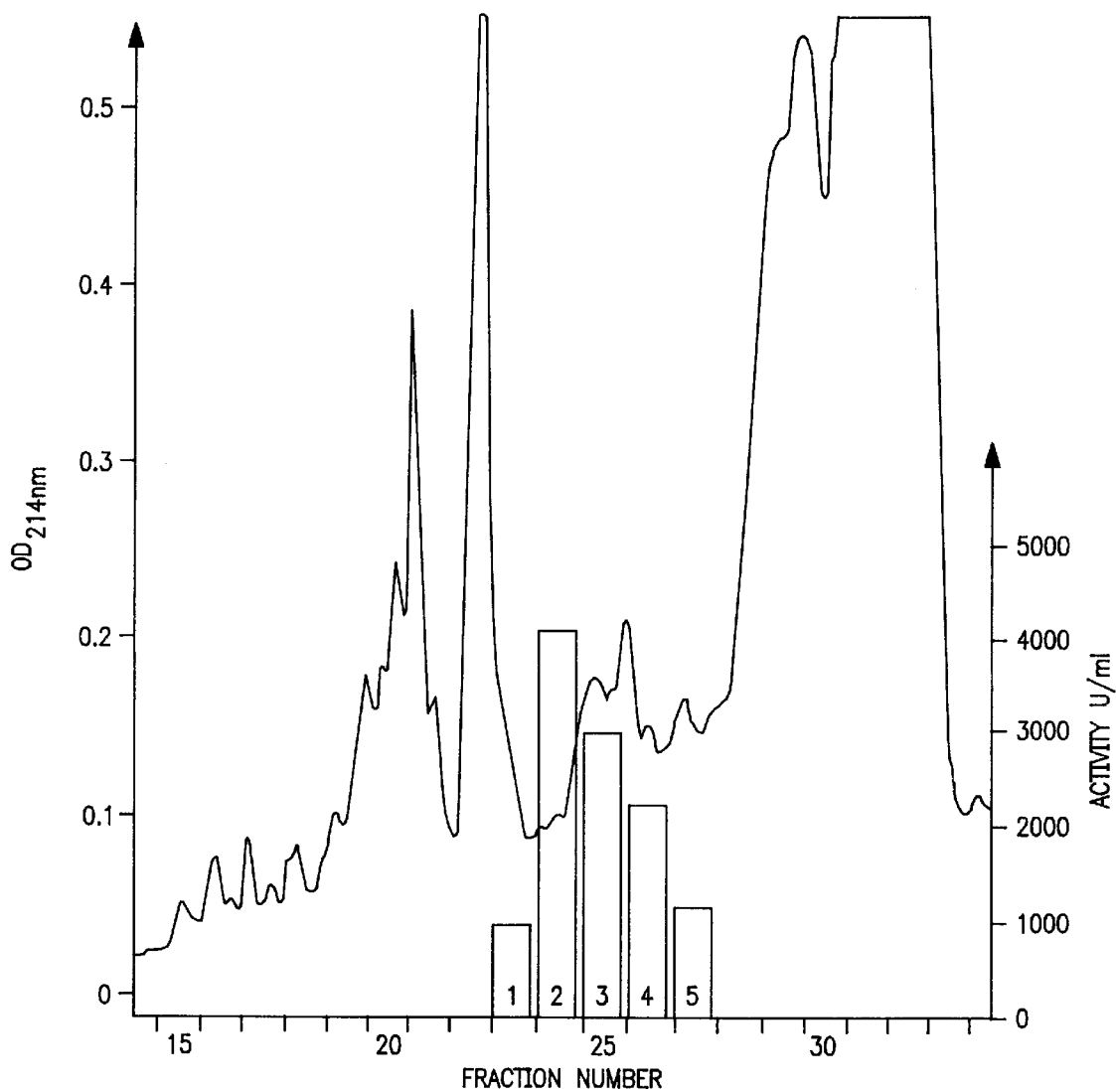
FIG. 1: Reversed phase chromatography (RPC) of AR97-187 preparation displaying the mitogenic activity of the fractions as tested in a Balb/MK TIA.

Primary human keratinocytes were isolated by trypsin treatment of meshed split-thickness skin specimens essentially as described by Rheinwald and Green (Cell 6, 331–344, 1975). Cells were seeded in 175 cm$^2$ Falcon flasks on mitomycin C-treated 3T3 feeder layers at a density of 28,000 cells/cm$^2$ in the following medium (called MCEC-tot): DMEM/Ham's F12 (3/1), 10% inactivated fetal calf serum, 10 ng/ml mouse EGF, 0.4 μg/ml hydrocortisone, 9 ng/ml cholera toxin, 5 μg/ml transferrin, 5 μg/ml insulin, 2 pM triiodothyronine and 0.18 mM adenine. At confluence, keratinocytes were trypsinized and re-seeded at 1/3 dilution for secondary passage. For the preparation of conditioned medium, confluent multilayered epithelial sheets were used, usually at the end of passage two. The same sheets are routinely used for the treatment of burn patients.

2. Preparation of Conditioned Medium

At the end of the culturing period, stratified epithelial sheets were washed three times with PBS and transferred to MCEC-tot medium without serum, EGF, cholera toxin, transferrin, triiodothyronine, insulin, hydrocorisone and adenine. After 24 hours at 37° C., this conditioned medium was collected and stored at −20° C. until used for purification. In total, approximately 70 l of CM has been collected for purification purposes.

3. Bioassays

Balb/Mk Tia

This assay measures mitogenicity of the test factor by measuring incorporation of tritium-labeled thymidine into murine Balb/MK keratinocytes.

Balb/MK keratinocytes (Weissman and Aaronson, Cell 32, 599–606, 1983) are seeded in 48-well tissue culture plates in SMEM supplemented with 10% inactivated FCS, 5 ng/m EGF, 0.05 mM CaCl$_2$, and 0.02 mM calcium pantothenate at a density of 20,000 cells/well. After 24 h, the medium is replaced with 400 μL SMEM/F12 (7/1) containing the following additives: 0.2 mM ethanolamine, 10 nM sodium selenite, 5 μg/ml transferrin and 5 μg/ml insulin. After 24 h, the medium is removed and replaced by 300 μL SMEM/F12 (7/1) containing the same additives and 100 μl of test factor. After 24 h, 2 μCi of tritiated thymidine is added. Six hours later, the cells are harvested by trypsin treatment and the amount of incorporated label is determined by standard methods. In this assay, 1 ng/ml of EGF is used as a positive control. In this assay, one unit of bioactivity is defined as the amount of activity resulting in the same amount of incorporated label as 1 ng/ml of EGF.

Balb/3T3 TIA

This assay measures incorporation of tritiated thymidine into Balb/3T3 fibroblast cells (ATCC CCL-163). This cell line is unresponsive to the amphiregulin subforms starting at residues 101 and 107 of the preprotein (Shoyab et al., Proc. Natl. Acad. Sci. U.S.A 85, 6528–6532, 1988). The assay is performed essentially as described above for the Balb/MK TIA, exept that the cells are seeded in 96-well plates at a density of 5000 cells/well in 200 μl DMEM (Gibco-BRL, cat No. 32600–083) containing 2% inactivated newborn calf serum. After 24 h the medium is replaced by 150 μl DMEM/F12 (F12: Gibco BRL No. 21700–091) without serum and the test sample (50 μl) is added. After 24 hours, 1 μCi tritiated thymidin is added and 6 h later the cells are harvested and incorporated radiolabel is measured.

FBHEC TIA

This assay measures incorporation of tritiated thymidine in fetal bovine heart endothelial cells (FBHEC, ATCC CRL 1395). Cells are seeded in 96-well plates precoated for 10 min with 0.1% gelatin, at a density of 1000 cells/well in 100 μL DMEM with 20% FCS. After 6 h, 100 μl of the sample is added and 64 hours later the medium is removed and replaced by 200 μl of DMEM containing 10% FCS and 0.5 μCi of tritiated thymidine. Six hours later, the cells are havested and incorporated radioactivity is measured.

NRK-49F TIA

This assay measures incorporation of tritium thymidine in NRK-49F (ATCC CRL 1570) cells.

NRK49 cells are seeded in 48-well plates at 12,500 cells/well in 500 μl DMEM +10% fetal calf serum and incubated at 37° C. for 72 h. The medium is changed by 500 μl DMEM/F12 (1/1) containing 30 nM sodium selenite and 10 μg/ml transferrin. After 24 h the medium is removed and 400 μl DMEM/F12 (1/1) containing 30 nM sodium selenite, 10μg/ml transferrin, 5 μg/ml insulin, 1μM retinoic acid and 0.01% BSA. 100 μl sample is added (final dilution 1/5).

After 45h, 0.5 μCi tritium thymidine is added. After 2 h of incubation at 37° C., the cells are trypsinized and the amount of incorporated label measured.

COLONY FORMATION ASSAY OF NRK-49F CELLS IN SOFT AGAR

This assay measures the number of colonies formed by NRK-49F when seeded at low density in soft agar gels.

One ml of a solution of 0.5% agar made up in DMEM containing 10% Fetal calf Serum and non-essential amino acids is poured in a well of a 6-well plate at 37° C. and allowed to gel at room temperature. On top of this, a 1 ml top layer of the following composition is poured at 37° C.: 0.3% agar made up in DMEM, 10% Fetal Calf Serum and non-essential amino acids and containing 3500 NRK-49F cells and 100 μl of the test sample. After gelling at room temperature, the well is incubated at 37° C. for 7 to 8 days. After this incubation period, colonies of more than five cells are scored by microscopical analysis.

4. Purification of AR97–187
Chromatograph Procedures

One hundred and fifty L conditioned media from human keratinocytes was collected and stored at −20° C. until further processing. All the purification procedures were done at 4° C., except where indicated. Chromatography fractions were stored in all cases during the bioassay at −70° C. and were thawed and pooled just before the next processing step.

Purification on Hydroxylapatite

Ten L conditioned media batches were thawed and cleared by filtration (0.22 μm, Millipore). Phosphate and CHAPS were added till a final concentration of resp. 10 mM and 0.05% (w/v). The pH of the media was adjusted to pH 7.3 and the solution was applied at a rate of 30 cm/h on a 80 mL Biogel HTP (Biorad), which was equilibrated with 10 mM $K_2HPO_4/KH_2PO_4$, 0.1% (w/v) CHAPS, pH7.3. The column was washed with 125 mL equilibration buffer and the bound proteins were desorbed at a rate of 15 cm/h by applying a stepwise gradient: 300 mL 50 mM phosphate, 350 mL 200 mM phosphate and 400 mL 400 mM phosphate. The resin was regenerated with 400 mL 500 mM phosphate, pH 7.3, CHAPS 0.1%. The eluate was collected in 10 mL fractions, samples were diluted 12-fold in 20 mM HEPES,pH 7.2, 150 mM NaCl and assayed in the Balb/MK TIA at a 1/48 and 1/96 dilution.

Chromatography on Poros Heparin

Bioactive fractions of the 200 mM phosphate elutions were pooled and diluted four times with 20 mM HEPES, 0.1% (w/v) CHAPS, pH 7.2 (buffer A). A sample equivalent to 12 L conditioned medium was loaded at a rate of 153 cm/h on a 4 mL Poros Heparin column (50 μm beads, Perseptive Biosystems), previously equilibrated with buffer A. The resin was washed with five column volumes of buffer A, containing 150 mM NaCl. Heparin bound proteins were eluted at a rate of 76 cm/h by applying a NaCl-gradient in buffer A: (i) linear gradient from 150 mM to 750 mM in eight column volumes; (ii) wash with 750 mM in two column volumes and (iii) step gradient with 1M NaCl in three column volumes. The resin was regenerated with buffer A, containing 3M NaCl. One-mL fractions were collected, samples for bio-assay were diluted 60 times with PBS and tested in the assay in 1/240 and 1/480 dilution.

Chromatography on Strong Cation Exchanger (PorosHS)

Bioactive fractions, eluting at 650–750 mM NaCl from the Heparin chromatographies, were pooled. An amount corresponding to 17 L conditioned medium was diluted four times with buffer A and loaded at 360 cm/h on a 900 μL Poros HS column (20μ beads, Perseptive Biosystems). The column was washed with three column volumes buffer A containing 100 mM NaCl. Bound proteins were eluted at 150 cm/h by applying a linear salt gradient from 100 mM to 1M NaCl in buffer A, in ten column volumes. Wash and elution were run on the SMART system (Pharmacia) and 500 μL-fractions were collected. Bio-assay samples were diluted 120 times in PBS and were assayed at a dilution of 1/480 and 1/960.

Chromatography on Weak Cation Exchanger(HEMA CM)

Bioactive fractions, eluting at 650 to 900 mM NaCl on the Poros HS were pooled and diluted seven times with buffer A. A sample equivalent to 30L of conditioned medium was loaded at a rate of 180 cm/h on a 800 μL weak cation exchange HPLC column (HEMA IEC BIO CM,4.6×50 mm) (Alltech). The column was washed with one column volume buffer A containing 100 mM NaCl and eluted with a linear gradient from 100 mM to 1M NaCl in buffer A, using ten column volumes. Wash and elution were run on SMART system (Pharmacia) and 200 μL-fractions were collected in tubes precoated with 1% (w/v) CHAPS. Two and a half μL was diluted in PBS and used for the Balb/MK bio-assay at a final dilution of 1/960 and 1/1920.

Microbore Reversed Phase Chromatography

Bioactive fractions eluting from the HEMA CM HPLC column were pooled and TFA was added to 0.1% (v/v). A sample corresponding with 6 L of conditioned medium was loaded at 60 cm/h on 75 μL microbore reversed phase $C_8$ columns (0.8×150 mm, LC Packings), which contained Zorbax $C_8$(5μ beads) as support. The columns were washed with three column volumes equilibration buffer (0.1%(v/v) TFA in MQ) and eluted by applying a linear gradient from 0 to 100% ACN in equilibration buffer, using forteen column volumes. Twenty-μL fractions were collected in 40 μL neutralising buffer (20 mM HEPES, pH7.2) in CHAPS-precoated eppendorf tubes. Two-μL bio-assay samples were diluted in PBS and tested in the Balb/MK bioassay at a 1/1200 and 1/2400 final dilution. Chromatography was performed on the SMART system (Pharmacia). Active fractions eluted between 21 and 27% ACN. A representative elution profile from one of the RPC runs is presented in FIG. 1.

In total, an amount equivalent to 51L of CM has been purified by RPC, yielding a total of 6973 Units of activity in the Balb/MK assay.

5. PAGE, Mass Analysis, Sequencing

SDS/Polyacryl Amide Gel Electrophoresis

SDS-PAGE was performed according to Shagger and Von Jagov (An.Bioch. 166,368–379,1987) with the following minor modification: separating gels were prepared with 15% acrylamide/bisacrylamide-solution. Sample buffer consisted of 4%(w/v) SDS, 12%(v/v) glycerol, 0.05M Tris/HCL pH6.8, 0.01%(w/v) Bromophenol blue. Protein samples, precipitated or lyophilised were resuspended in sample buffer with or without 100 mM DTT and boiled for five minutes. The proteins were loaded onto 0.75 mm gels (15×12 cm) and separated electrophoretically until the tracking dye had reached the bottom of the gel. Proteins were visualised with the silverstaining method according to Heukeshoven and Dernick (Electrophoresis, 1988 9:203–209). Alternatively, proteins were loaded on the PHAST-system (Pharmacia) using 1μL–4μL slots and separated on 20% homogeneous precast gels. After electrophoresis proteins were stained according to the same method as mentioned above.

Figure 2:
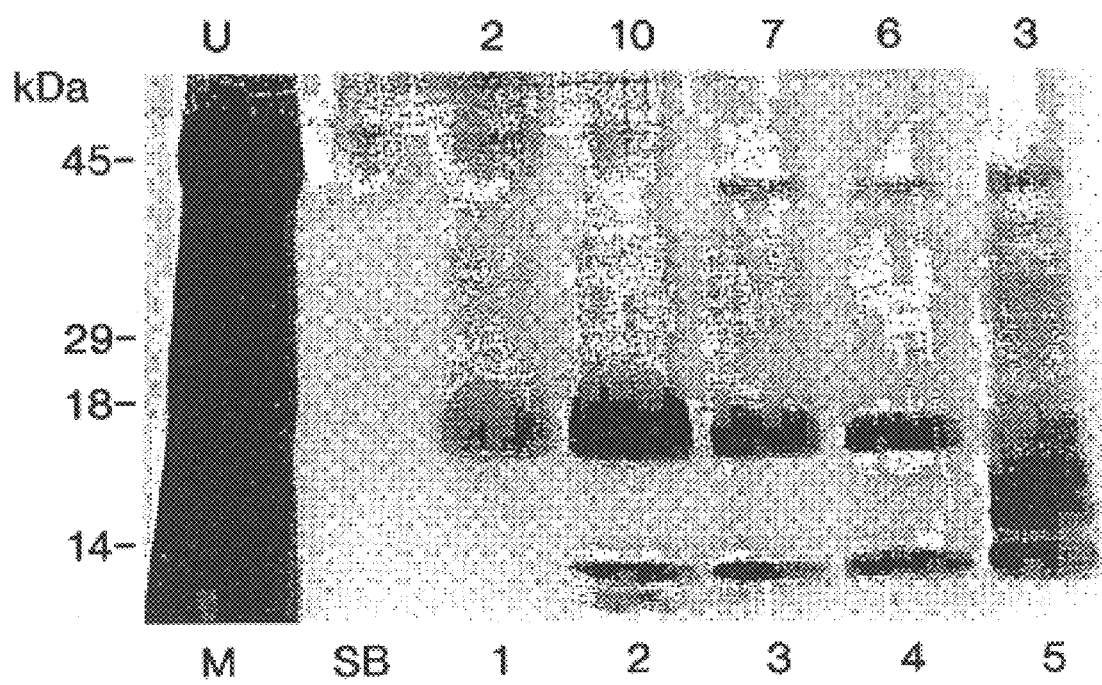
FIG. 2: SDS-PAGE of RPC-8-purified AR97-187 preparation. Proteins eluted from Zorbax the C8 column were dried in a Speed-vac, resolubilized in sample buffer containing 100 mM DTT. Samples were electrophoresed on 20% precast SDS-acrylamide gels on the PHAST system. Protein bands were visualized by silver staining. The amount of mitogenic activity (as observed in the Balb/MK assay and expressed as units, see example 3) is printed above each lane.

Active fractions from the RPC run were pooled as indicated in FIG. 2 (pools 1 to 5) and analysed on SDS-PAGE as described above. Results (FIG. 2) show that activity correlates mainly with a 17–18 kDa doublet, with additional bands being present at 45 kDa and 6–4 KDa. The 45 kDa band does not correlate with bioactivity, while the 6 kDa band may also be bioactive, albeit much less than the 17–18 k-Da bands.

Protein Dosages

Protein concentrations were determined by the Coomassie Brilliant Blue G-250-binding method as described by M. M. Bradford (An.Bioch. 72,248–254,1976). Protein samples(50 μL) were diluted in 750 μL Bradford solution (0.01%(w/v) Coomassie Brilliant Blue G-250 (Sigma), 4.7%(w/v) Ethanol (Merck) and 8.5%(w/v) Phosphoric acid (Merck)),and were made up to 1250 μL with MQ-water in 1.5 mL disposable cuvettes (Brand). Contents were mixed by inversion and the absorbance was measured at 595 nm against blank reagents in a UV-VIS 1205 spectrophotometer (Shimadzu). The protein concentrations were determined by linear regression from a Bovine Serum Albumine-standard curve ranging from 25 to 750 μg/mL. The calibration protein was prepared in PBS.

Mass Spectrometry of Bioactive Pools

Pooled biocative fractions (see FIG. 2) were analysed by matrix-assisted laser desorption ionisation mass spectrometry (MALDI). In the most active pool (pool 2,), main mass peaks were detected at 12937, 11776, 6780 and 5806 Da. These masses correspond likely to the 17–18 and 4–6 kDa doublets observed on SDS-PAGE. The discrepancy between the migration on SDS-PAGE at 17–18 kDa and the spectrometrically observed mass profiles is probably related to an abnormally slow migration of amphiregulin on SDS-gels. A similar discrepancy between the mass of AR as measured by SDS-PAGE versus gel filtration was also reported by Shoyab et al. (Proc. Natl. Acad. Sci. USA 85, 6528–6532, 1988).

Mass Spectrometry of Tryptic Peptides

After the last purification step, different protein bands were still observed on SDS-PAGE. Because it proved difficult to purify these until homogeneity by chromatographical means, it was decided to isolate the different bands from preparative SDS-PAGE gels. Bioactive fractions from the RPC-chromatographies were pooled, SDS and DTT were added to 0.04% (w/v) and 2 mM respectively, and the mixture was incubated for 1 h at room temperature. The sample was concentrated 100 times using a speedvac, resuspended in sample buffer(without SDS) and boiled for five minutes under paraffin oil. Used eppendorfs were regenerated in 200 μL 80% (v/v) ACN-0.1 (v/v) TFA to recover a specific adsorbed protein and treated as above. The sample was loaded on the PHAST-system (Pharmacia) and the separated protein bands were visualised by Coomassie Brilliant Blue staining.

Two zones were cut from these gels: the zone containing the 17–18 kDa doublet and the zone containing the 6 kDa band. Acrylamide fragments containing these bands were subsequently subjected to trypsin digestion, a protease which cuts after Lysine or Arginine residues (exept when these residues are followed by Proline). Tryptic peptides were subsequently eluted from the gel slices and about 1/500 of the eluted material mass was used for mass spectrometry analysis. This yielded the following masses (after elimination of mass values that could be ascribed to trypsin auto-digestion peptides):

for the 17–18 kDa doublet: 1161, 1595, 2316, 2450, 2610, 4313, 4727, 8616. for the 6 kDa band: 568, 1160, 1301, 1325, 1596, 1695, 2083, 2323, 2470.

Amino Acid Sequencing of Tryptic Peptides

Tryptic peptides eluted from the gel slices where separated on a C4 Vydac (1 mm×250 mm) RPC column. Several separated peptide peaks were subsequently subjected to automated Edman degradation on an Applied Biosystems 477A sequenator. The peptide sequences attributable to amphiregulin isoforms obtained are given in Table 1.

Figure 3:
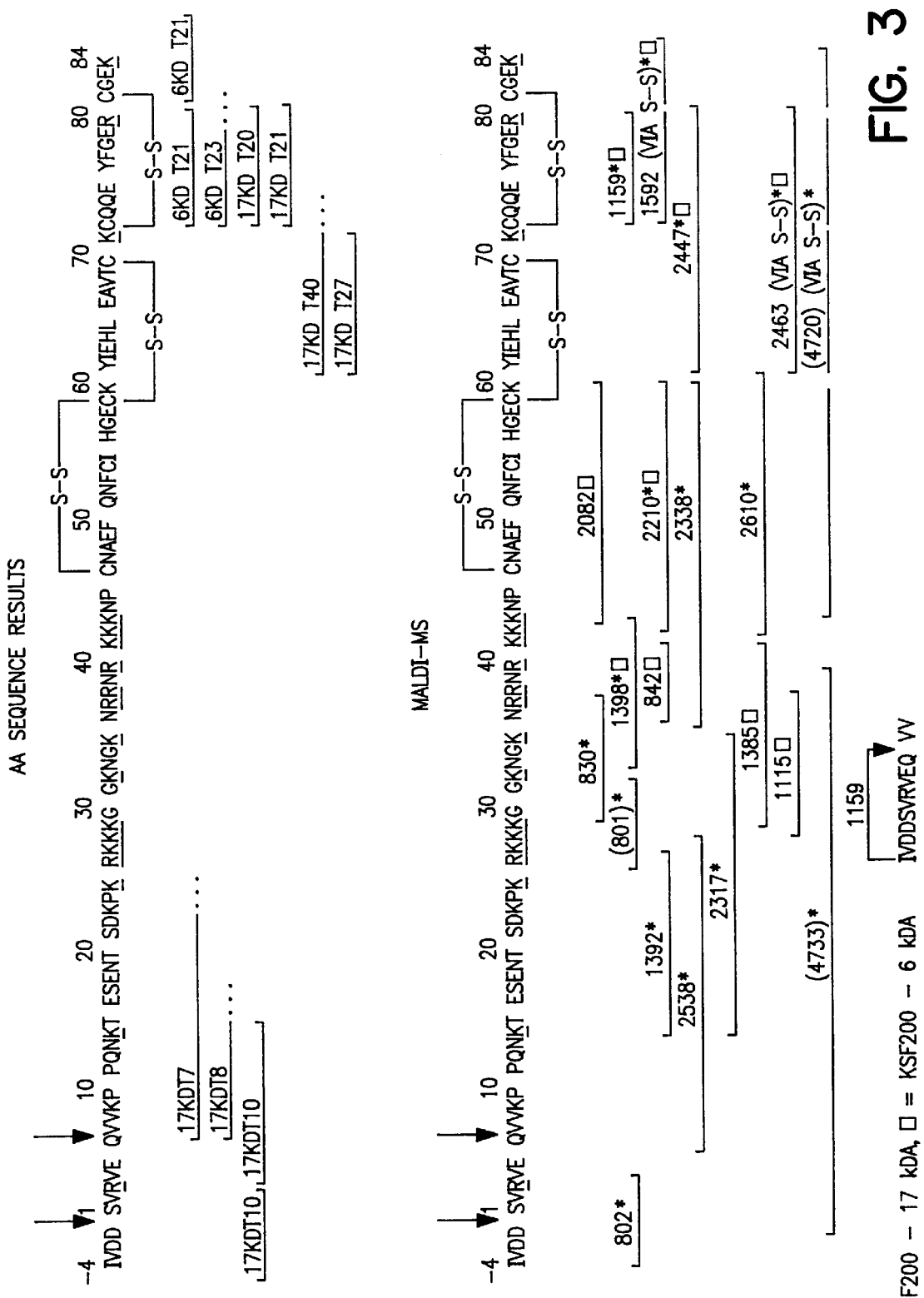
FIG. 3: Summary of the amino acid sequencing and mass analysis data. The total predicted amino acid sequence of AR97-187 is shown in FIG. 3a. Tryptic peptides from the 6 and 17 k-Da bands are indicated by continuous lines and the name of the peptide. Theoretical tryptic peptides from which a mass signal was obtained by MALDI are indicated in FIG. 3b, together with their theoretical mass. Peptides from which a mass signal was obtained during Maldi on the 17 kDa band are indicated with a #, peptides from which a mass signal was obtained during MALDI on the 6 KDa band are indicated with a *. See also Table II for a summary of the MALDI data.

A summary of the amino acid sequencing data is represented in FIG. 3.

Several RPC-purified peptides were also subjected to MALDI. The results of this analysis are shown in Table 2:

Interpretation of the Results

The 17–18 kDa doublet

As judged from the combination of SDS-PAGE and biological activity data, the main biological activity is correlated with the doublet migrating at 17–18 kDa.

TABLE 1

| For the 17 kDa doublet:: |
| --- |
| T7: VVKPPQXKTESXNTSDX (SEQ ID NO 2) |
| T8: VVKPPQXKT (SEQ ID NO 3) |
| T10: IVDDSV(R) (minor sequence; SEQ ID NO 4) |
|     VEQVVKPPQXK (main sequence; SEQ ID NO 5) |
| T20: XQQEYFGE (SEQ ID NO 6) |
| T21: (Q)XQQEYFGE (SEQ ID NO 7) |
| T40: YIXXLXXAXTX(K) (SEQ ID NO 8) |
| T27: YIEXLEAVT (SEQ ID NO 9) |
| For the 6 kDa band: |
| T21: XQQEYFGE (main sequence; SEQ ID NO 10) |
|     GEK (minor sequence) |
| T23: XXQXEYFGE (SEQ ID NO 11) |

Legend Table 1: peptide sequences found after trypsin digestion and peptide sequencing of eluted proteins present in the 17 and 6 kDa bands.

TABLE 2 peptide masses obtained from the 17 kDa band:
Trypsin digest mix 1161 (AH); 1595 (AH); 2167 (TB); 2214 (AH + TP); 2286, 2278 (TB); 2316 (AH); 2467 (AH + TP); 2610(AH); 4313; 4727 (AH)?; 8616
Tryptic, peptides after HPLC separation of digest mix T7
T10    804 (AH)
T16
T19    1046; 1160 (AH); 1209;; 1363; 1595 (AH)
T20    1062; 1162 (AH); 1180; 1211
T21    1160(AH)
T24
T27    835 (AH); 1129; 1356; 1397 (AH)
T29    872; 1160 (AH); 1309; 1378; 1395 (AH); 1478; 2459; 2538 (AH)
T36    1325; 1814; 2548 (TP)
T40    2168 (TB); 2450 (AH)
T42
T44
T46    1740; 2213 (AH + TP), 2234; 2251
T47
T48
T50    2292
T51    2295
T55
T57    1327; 1476; 1571; 1634; 1816; 2090 (TP); 2338 (AH)
peptide masses obtained from the 6 kDa band:
Trypsin digest mix:

568; 991 (LC); 1047 (LC); 1160 (AH); 1301; 1325; 1360 (LC); 1434 (LC); 1596 (AH); 1695; 1757 (LC); 2683 (AH); 2167 (TB); 2214 (AH + TP); 2278 (TB); 2323; 2470
Tryptic peptides after HPLC separation of digest mix:

T6
T8     1794
T11    607; 998
T12
T13    660
T16
T17
T19    1047 (LC); (1249); 1505
T21
T23
T25    481
T26    1128; 1329; 1742
T28    843 (AH); 1127; 1358
T30
T32    878; 894
T37    991; 1007; 2001; 2467 (AH + LC + TP)
T42    1711; 1726; 2167 (TB); 2448 (AH)
T43    1093; 1171; 1357; 1376; 1403; 1439; 1649; 1696; 1712
T44    1695; (1711)
T46    1710; 1725; 2213 (AH + TP)
T47    1115; 1483; 1712; 1725
T48    1323
T51    1681; 1696; 1712; 2280 (LC); 2296

Legend table 2:
molecular masses of peptides obtained after trypsin digestion of the proteins present in the 17 kDa and 6 kDa bands, either before or after separation of individual peptides by HPLC. Peptide masses which correspond with theoretical tryptic peptides derived from bovine trypsin, porcine trypsin; chicken lysozyme and human amphiregulin are printed in bold and indicated with TB, TP, LC and AH, respectively.

MALDI-MS analysis indicates that the true size of these bands is 11776 and 12937 Da, respectively.

Amino acid sequencing shows that most of the tryptic peptides derived from these protein bands correspond to human amphiregulin sequences as published by Shoyab et al. (Science 243, 1074–1076, 1989). However, the sequence of one peptide (peptide T10 with sequence IVDDSV(R); SEQ ID NO 4) starts at a position located 4 amino acids earlier than the longest amphiregulin isoform published thus far (the isoform starting at residue 101 of the preprotein with the sequence SVRVEQ (SEQ ID NO 12). MALDI-MS of this peptide peak indicates a molecular mass of 804 Da, which corresponds closely with the theoretical mass of this peptide (802 Da). Since the N-terminal end of this peptide T10 does not correspond with a trypsin recognition site (the sequence of the propeptide in this region is: . . . QIPGY↓IVDDSVR. . . (SEQ ID NO 13), where ↓ indicates the putative cleavage site), one must conclude that it corresponds with the natural N-terminal end of a new form of amphiregulin. This new form, which is called AR97-187 in the present application, may contain at least 90 amino acids and starts at a position 4 amino acids earlier than the isoform starting at residue 101 mentioned above.

In addition, we also detect tryptic peptides (peptide T7 with sequence VVKPPQXKTESXNTSDX (SEQ ID NO 2) and peptide T8 with sequence VVKPPQXKT (SEQ ID NO 3)) corresponding with the shortest amphirezulin isoform thus far published (the isoform starting at residue 107of the preprotein, with the sequence VVKPPQ (SEQ ID NO 14); Shoyab et al., Science 243, 1074–1076, 1989).

The identity of the 17–18 kDa doublet with these two amphiregulin isoforms is also confirmed by the MALDI-MS data obtained on the undigested 17–18 doublet. This showed the mass of these two proteins to be 11776 and 12937 Da, respectively. The difference between these two masses (1161 Da) corresponds closely with the theoretically calculated mass difference (1159 Da) between the isoform starting at residue 97 of the preprotein (AR97-187) and the isoform starting at residue 107 of the preprotein. This difference also corresponds with the observed mass difference between the 17 and 18 kDa bands observed on SDS-PAGE. Since both bands on SDS PAGE are of approximately identical intensity, and since the 11776 Da and 12937 Da MALDI MS signals are also of similar intensity, we conclude that AR97-187 and the isoform starting at residue 107 of the preprotein are present in approximately equimolar amounts in our samples.

The sequence NKT at position 14 in SEQ ID NO 1 corresponds with a putative N-glycosylation site. The fact that the N residue at position 14 was not detected during Edman sequencing of peptides T7, T8 and T10 indicates that this site is indeed glycosylated.

The 6 kDa Band

Edman sequencing indicates that the tryptic peptides of protein present in the 6 kDa band also correspond to amphiregulin sequences. Since the mass of this band (6780 Da on MALDI-MS and about 6 kDa on SDS-PAGE) is considerably lower than that of either one of the isoforms starting at residues 97, 101 or 107 of the preprotein, we conclude that it concerns a proteolytic degradation product of one of these amphiregulin isoforms. Probably, this degradation product is only slightly or not at all active, since its intensity on SDS-PAGE does not correlate with the amount of activity loaded on the gel. Presumably, this degradation product originates from one or more cleavage events in the Arg/Lys-rich region spanning residues 27–47 in SEQ ID NO 1.

6.In Vitro Biological Activity of AR97-187-Containing Preparations and Effect of Heparin on this activity Activity on Balb/MK Cells During purification, activity is followed by means of the tritium thymidine incorporation assay on murine Balb/MK keratinoctye cells.

Purification of 150 L of conditioned medium yielded a total of 10,000 U of activity, with an average specific activity of about 625 U/µg.

Cooke et al. (Mol. Cell. Biol. 11, 2547–2557, 1991) have demonstrated that the biological activity on this and other cell types of the hitherto known amphiregulin isoforms starting at residues 101 or 107 of the preprotein is nearly completely inhibited in the presence of heparin.

Figure 4A:
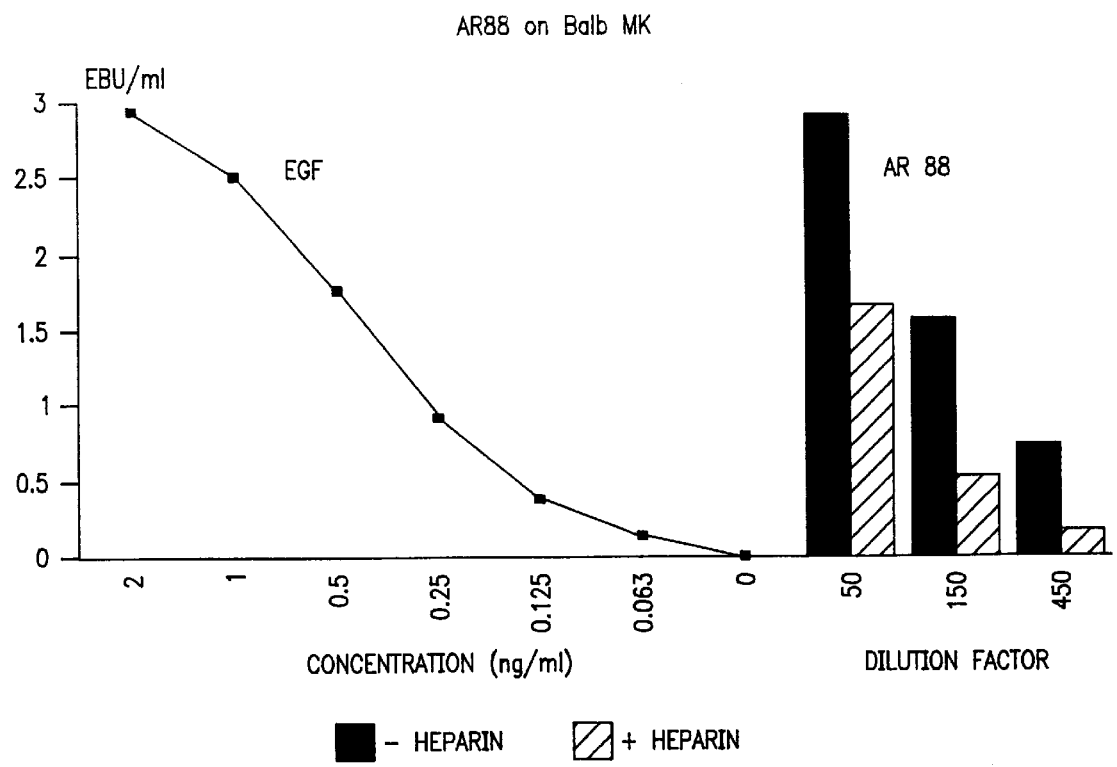
FIG. 4:
a) Activity of AR97-187 preparation (diluted 50-, 150- or 450-fold) in a Balb/MK TIA in presence and absence of heparin (10 μgml). For comparison, an EGF dose-response curve is also included.
b) Activity of an MCF-7-derived amphiregulin preparation (diluted 400- to 6400-fold) in a Balb/MK TIA in presence and absence of heparin (10 μg/ml). For comparison, an EGF dose-response curve is also included.
Figure 4B:
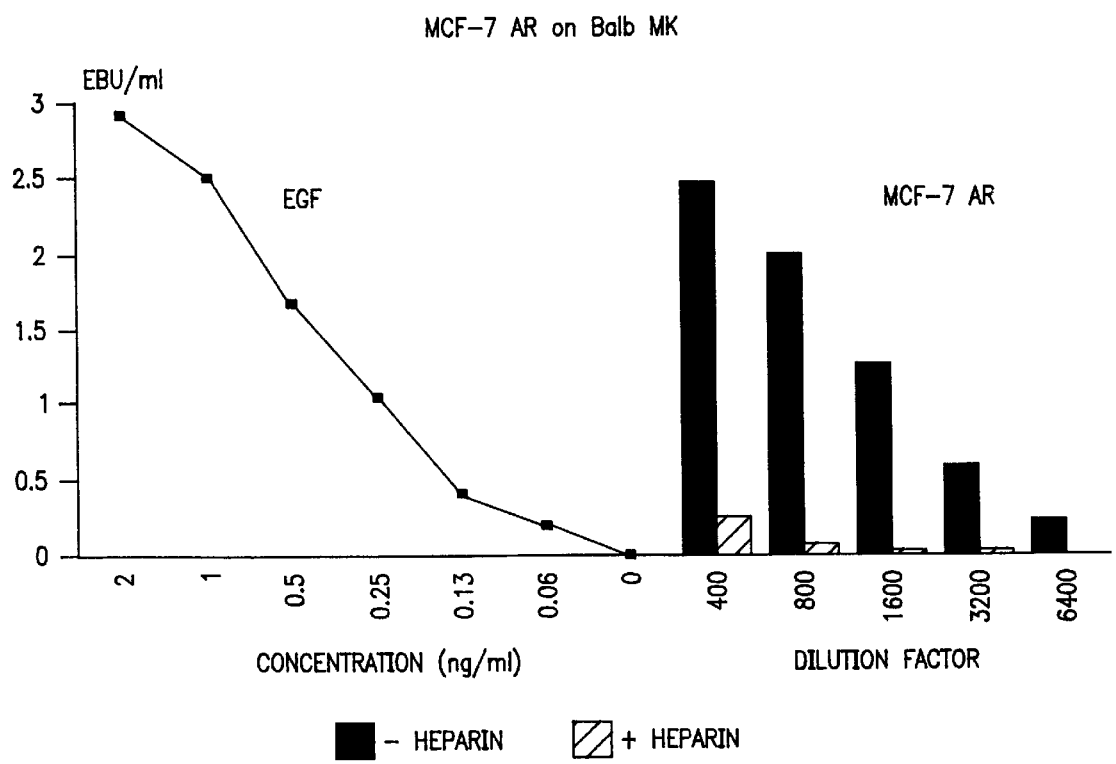

In contrast, the residual activity of our RPC-8-purified AR97-187-containing preparation in the presence of 10 µg/ml of heparin was between 21 and 57% of the activity in absence of heparin. As a control, we included a preparation of MCF-7-derived amphiregulin enriched by heparin chromatography (which contains the isoforms starting at residues 101 and 107 of the preprotein). As expected, the latter preparation was nearly completely inhibited (residual activity in presence of heparin between 0 and 10% of activity in absence of heparin) under the same assay conditions and over the same activity range, see FIG. 4a, b. This demonstrates that the heparin concentration in the assay was indeed sufficiently high to obtain complete blockage of the isoforms starting at residues 101 or 107 but not of the AR97-187 isoform. This shows that the mitogenic activity of the AR97-187 preparation is different from that of the already described amphiregulin isoforms.

Activity on FBHE Cells

The tritium thymidine incorporation assay on FBHE cells (ATCC CRL 1395) is considered of having a limited specificity for growth factors belonging to the FGF family (Van Zoelen, Prog. in Growth Factor Res. 2, 131–152, 1990). As expected, none of our AR97-187 preparations showed any activity in this assay.

Thritium Thymidine Incorporation of NRK Cells

Figure 5A:
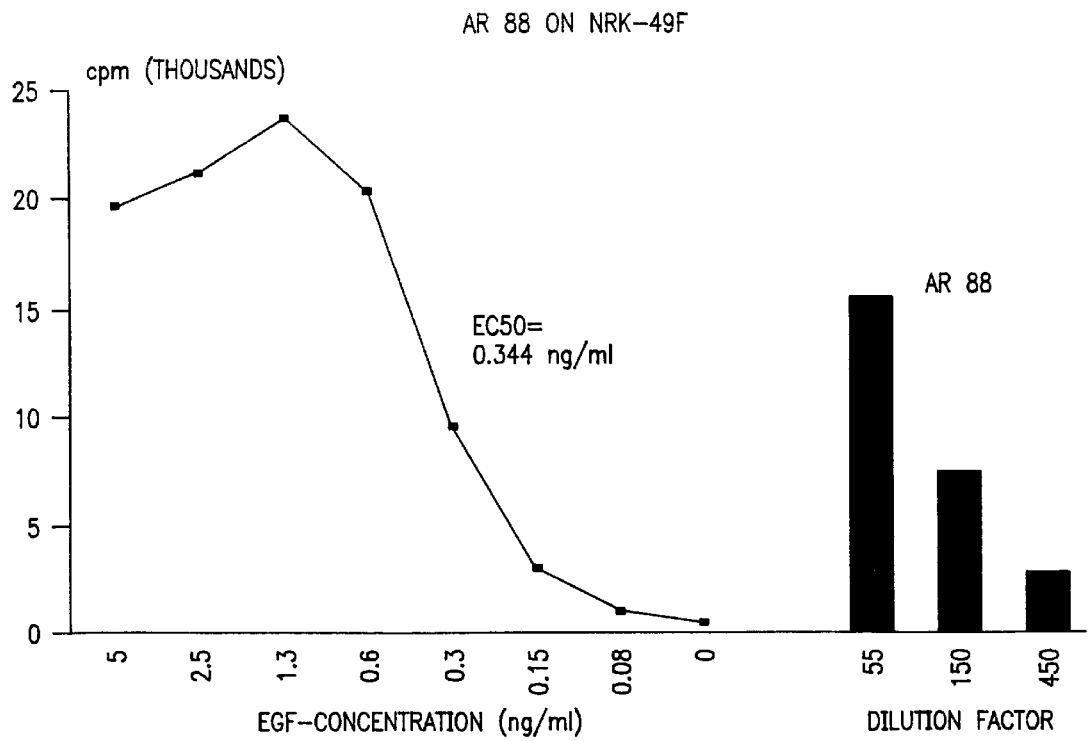
FIG. 5:
a) Activity of AR97-187 preparation (diluted 55-, 150- and 450-fold) in a TIA on NRK cells. For comparison, an EGF dose-response curve is also included.
b) Activity of a recombinant amphiregulin (rAR78, produced in E. coli) preparation in a TIA on NRK cells. For comparison, an EGF dose-response curve is also included.
Figure 5B:
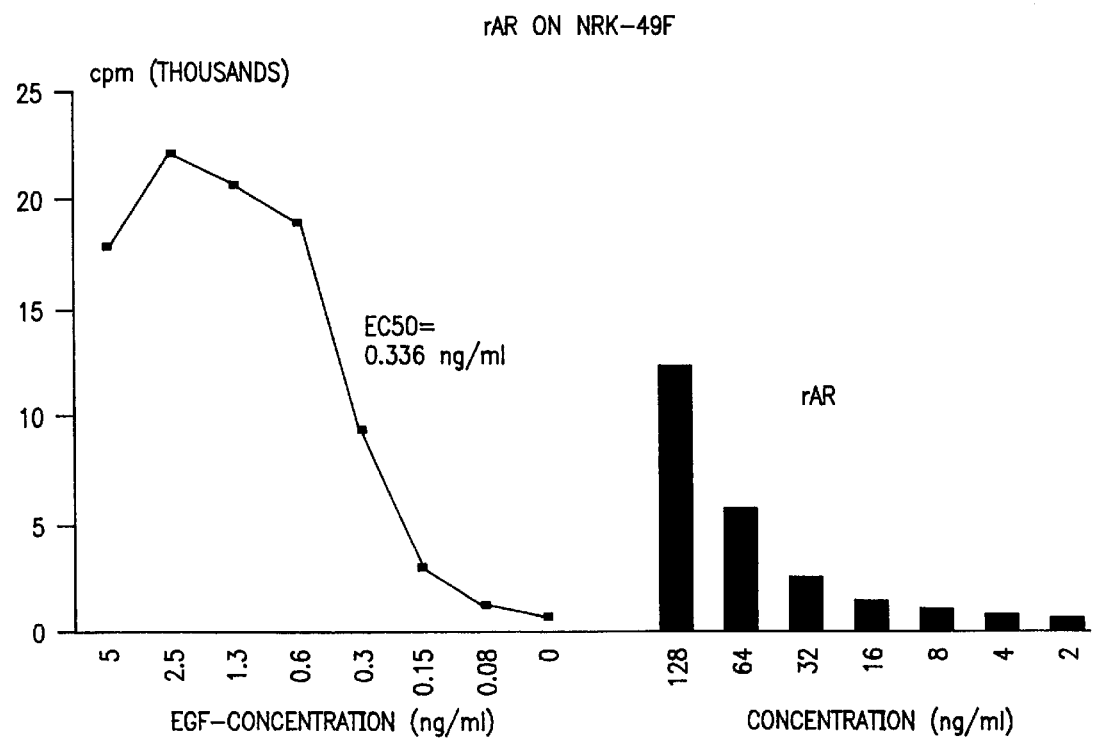

The amphiregulin isoforms starting at residues 101 and 107 have been reported to be active on normal rat kidney NRK-SA6 cells in a deoxyuridine incorporation assay (Shoyab et al., Pro,. Natl. Acad. Sci. U.S.A 85, 6528–6532, 1988). We have investigated the activity of both a recombinant 78 aa amphiregulin preparation (subform starting at residue 107 of the preprotein, produced in E. coli, R&D Systems No. 262-AR-100) and our AR97-187 preparation on NRK-49F cells, another normal rat kidney cell line, in a tritium thymidine incorporation assay. As a control, natural mouse EGF was used. FIG. 5 shows that both the recombinant AR and the AR97-187 preparation are mitogenic for these cells. Based on a comparison with the EGF curves, a 1/150 diluted AR preparation would contain an equivalent mitogenic activity as about 0.28 ng/ml of EGF. 8 ng/ml of the recombinant amphiregulin preparation contains an amount of mitogenic activity similar to about 0.309 ng/ml of EGF. This means that a 1/150 diluted AR97-187 preparation has a similar mitogenic activity of about 8 ng/ml of the recombinant amphiregulin preparation in this assay; a 1/50 diluted AR97-187 preparation would then correspond to 24 ng/ml of the recombinant 78 aa amphiregulin form.

Colony Formation of NRK Cells in Soft Agar

Figure 6:
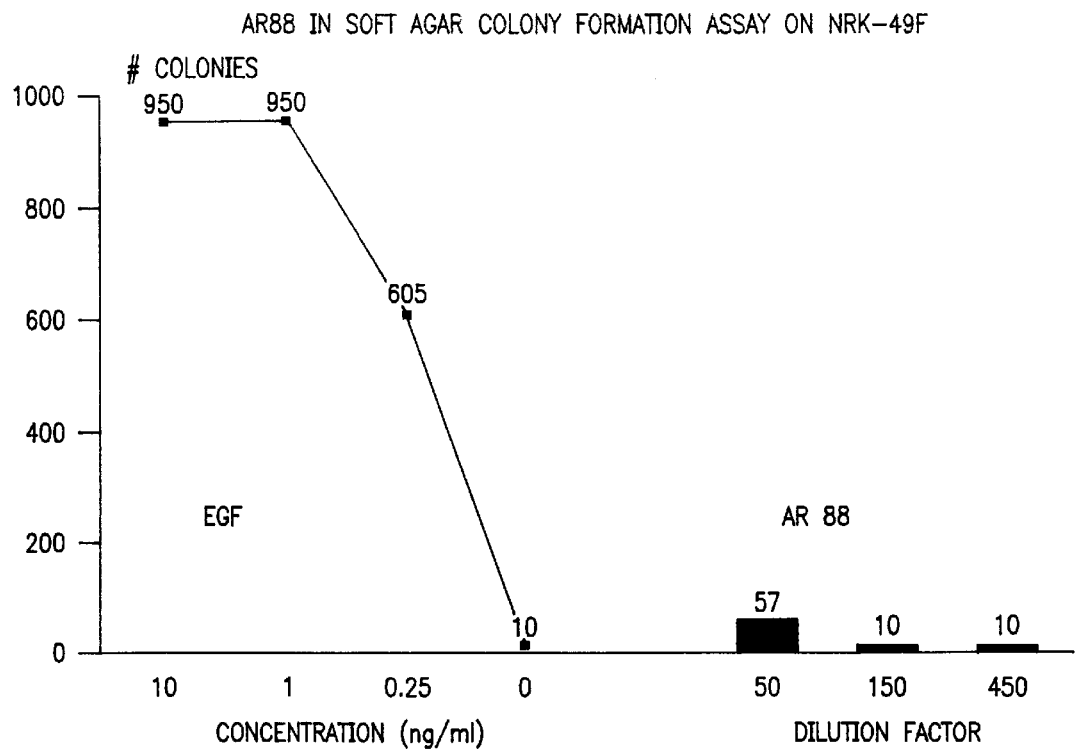
FIG. 6: Activity of a AR97-187 preparation (diluted 50-, 150- or 450-fold) in a soft agar colony formation assay on NRK cells. For comparison, an EGF dose-response curve is also included.

Shoyab et al (Science 243, 1074–1076, 1988) reported the amphiregulin subforms starting at residues 101 and 107 of the preprotein to be non-inducers of colony formation of NRK-SA6 cells. We have confirmed this for the recombinant 78 amino acid amphiregulin form (expressed in E. coli, R&D Systems No. 262-AR-100), which also did not induce colony formation of NRK49F cells within a range of 2 to 128 ng/ml. Our AR 88 preparation, on the contrary, significantly induced colony formation of these cells, albeit to a much lesser extent than EGF (FIG. 6). This confirms that the mitogenic properties of the AR97-187 form of amphiregulin are different than those of the amphiregulin subform starting at residue 101 of the preprotein.

Activity on Balb/3T3 Cells

According to Shoyab et al. (Proc. Natl. Acad. Sci. USA 85, 6528–6532, 1988), the 84 and 78 aa isoforms of amphireculin have no activity on murine Balb 3T3 fibroblasts.

To verify whether the AR97-187 is active on these cells, we have assayed an RPC-8-purified AR97-187 preparation in the Balb/3T3 TIA at dilutions ranging from 1/50 to 1/6400.

Figure 7:
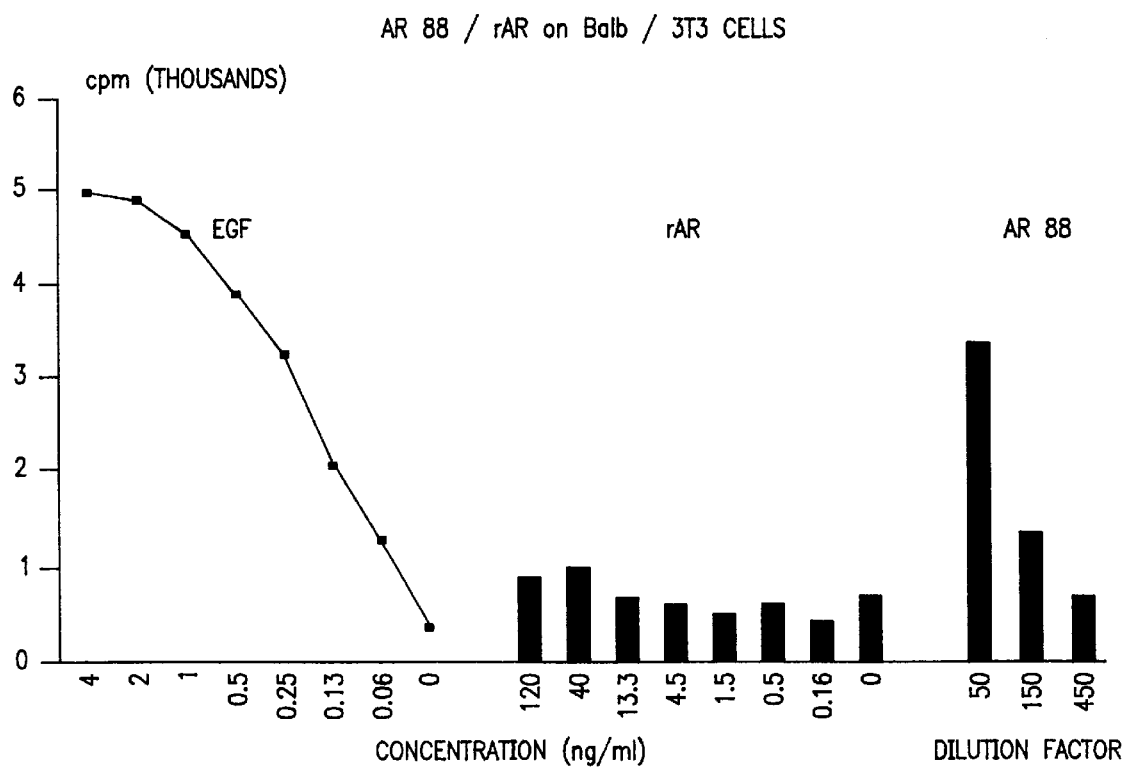
FIG. 7: Activity of a AR97-187 preparation (diluted 50-, 150- or 450-fold) and a recombinant amphiregulin preparation (rAR78, produced in E. coli) in a TIA on Balb/3T3 cells. For comparison, an EGF dose-response curve is also included.

As a control, a dilution curve of EGF at a concentration ranging from 0.063 to 4 ng/ml and a dilution curve of recombinant amphiregulin (78 amino acid isoform produced in E. coli, starting at residue 101 of the preprotein, R&D Systems No. 262-AR-100) at a range of 0.16 to 120 ng/ml was included. As shown in FIG. 7, the AR97-187 preparation produced a clear dose-response effect, indicating that AR97-187 is indeed active on Balb/3T3 cells, in contrast to the recombinant amphiregulin isoform and the abovementioned report on the other amphiregulin isoforms. Although 120 ng/ml of the recombinant amphiregulin preparation should contain 5 times more mitogenic activity as the 1/50 diluted AR97-187 preparation (based on comparison of both preparations in the NRK TIA, see above), it did not significantly stimulate the Balb/3T3 cells above control values.

What is claimed:

1. An isolated and purified polypeptide having heparin binding properties, said polypeptide comprising the amino acid sequence set forth in SEQ ID NO: 1.

2. Polypeptide according to claim 1 having a mitogenic activity for Balb/3T3 fibroblast cells, and/or Balb/MK keratinocytes, and/or NRK cells, and/or Swiss 3T3 fibroblasts.

3. Polypeptide according to claim 1 having a mitogenic activity which is not completely inhibited in the presence of heparin.

4. Polypeptide according to claim 1 wherein it elutes from a heparin column between about 0.5 and about 0.8 M NaCl.

5. Polypeptide according to claim 1 obtained from a keratinocyte cell medium or lysate.

6. Polypeptide according to claim 5, wherein said keratinocyte cells are human partially differentiated, stratified, multilayered keratinocytes.

7. An isolated and purified polypeptide comprising the amino acid sequence as represented in SEQ ID NO: 1, provided that said polypeptide has retained the surprising characteristics of its mitogenicity for BALB/MK cells and being less sensitive to heparin in demonstrating this effect.

8. An isolated and purified polypeptide comprising the amino acid sequence as represented in SEQ ID NO: 1.

9. An isolated and purified polypeptide according to claim 1 comprising the amino acid sequence as represented in SEQ ID NO 1, provided that said polypeptide contains the N-terminal sequence IVDDSVR of SEQ ID NO 1 preceded by the amino acid residue methionine.

10. A glycosylated polypeptide of claim 1.

11. An un-glycosylated polypeptide claim 1.

12. A fusion polypeptide that comprises a polypeptide of claim 1.

13. A composition for treating skin wounds comprising an effective amount of the polypeptide of claim 1 to effect healing of the skin wounds and an inert, pharmaceutical carrier.

14. An isolated polypeptide comprising the amino acid sequence of SEQ ID No: 1 produced by partially differentiated, stratified, multilayered human keratinocyte cell cultures.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 91 amino acids
        (B) TYPE: amino acid
        (C) STRANDEDNESS:
        (D) TOPOLOGY: linear (ii) MOLECULE TYPE: protein (iii) HYPOTHETICAL: NO (xi) SEQUENCE DESCRIPTION: SEQ ID NO: 1:

Ile Val Asp Asp Ser Val Arg Val Glu Gln Val Val Lys Pro Pro Gln
1               5                   10                  15

Asn Lys Thr Glu Ser Glu Asn Thr Ser Asp Lys Pro Lys Arg Lys Lys
            20                  25                  30

Lys Gly Gly Lys Asn Gly Lys Asn Arg Arg Asn Arg Lys Lys Lys Asn
        35                  40                  45

Pro Cys Asn Ala Glu Phe Gln Asn Phe Cys Ile His Gly Glu Cys Lys
    50                  55                  60

Tyr Ile Glu His Leu Glu Ala Val Thr Cys Lys Cys Gln Gln Glu Tyr
65                  70                  75                  80

Phe Gly Glu Arg Cys Gly Glu Lys Ser Met Lys
                85                  90

(2) INFORMATION FOR SEQ ID NO: 2:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: protein (iii) HYPOTHETICAL: NO (xi) SEQUENCE DESCRIPTION: SEQ ID NO: 2:

Val Val Lys Pro Pro Gln Xaa Lys Thr Glu Ser Xaa Asn Thr Ser Asp
1               5                   10                  15

Xaa (2) INFORMATION FOR SEQ ID NO: 3:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: protein (iii) HYPOTHETICAL: NO (xi) SEQUENCE DESCRIPTION: SEQ ID NO: 3:

Val Val Lys Pro Pro Gln Xaa Lys Thr
1               5

(2) INFORMATION FOR SEQ ID NO: 4:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: protein (iii) HYPOTHETICAL: NO (ix) FEATURE:
        (A) NAME/KEY: Modified-site
        (B) LOCATION:7
        (D) OTHER INFORMATION:/note= "UNSURE AMINO ACID"

(xi) SEQUENCE DESCRIPTION: SEQ ID NO: 4:

```
Ile Val Asp Asp Ser Val Arg
1               5
```

(2) INFORMATION FOR SEQ ID NO: 5:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: protein (iii) HYPOTHETICAL: NO (xi) SEQUENCE DESCRIPTION: SEQ ID NO: 5:

```
Val Glu Gln Val Val Lys Pro Pro Gln Xaa Lys
1               5                   10
```

(2) INFORMATION FOR SEQ ID NO: 6:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: protein (iii) HYPOTHETICAL: NO (xi) SEQUENCE DESCRIPTION: SEQ ID NO: 6:

```
Xaa Gln Gln Glu Tyr Phe Gly Glu
1               5
```

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: protein (iii) HYPOTHETICAL: NO (ix) FEATURE:
        (A) NAME/KEY: Modified-site
        (B) LOCATION:1
        (D) OTHER INFORMATION:
            /note= "UNSURE AMINO ACID"

(xi) SEQUENCE DESCRIPTION: SEQ ID NO: 7:

```
Gln Xaa Gln Gln Glu Tyr Phe Gly Glu
1               5
```

(2) INFORMATION FOR SEQ ID NO: 8:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: protein (iii) HYPOTHETICAL: NO (ix) FEATURE:
        (A) NAME/KEY: Modified-site
        (B) LOCATION:12
        (D) OTHER INFORMATION:
            /note= "UNSURE AMINO ACID"

(xi) SEQUENCE DESCRIPTION: SEQ ID NO: 8:

```
Tyr Ile Xaa Xaa Leu Xaa Xaa Ala Xaa Thr Xaa Lys
1               5                   10
```

(2) INFORMATION FOR SEQ ID NO: 9:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: protein (iii) HYPOTHETICAL: NO (xi) SEQUENCE DESCRIPTION: SEQ ID NO: 9:

```
Tyr Ile Glu Xaa Leu Glu Ala Val Thr
1               5
```

(2) INFORMATION FOR SEQ ID NO: 10:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: protein (iii) HYPOTHETICAL: NO (xi) SEQUENCE DESCRIPTION: SEQ ID NO: 10:

```
Xaa Gln Gln Glu Tyr Phe Gly Glu
1               5
```

(2) INFORMATION FOR SEQ ID NO: 11:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: protein (iii) HYPOTHETICAL: NO (xi) SEQUENCE DESCRIPTION: SEQ ID NO: 11:

Xaa Xaa Gln Xaa Glu Tyr Phe Gly Glu

```
(2) INFORMATION FOR SEQ ID NO: 12:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: protein (iii) HYPOTHETICAL: NO (xi) SEQUENCE DESCRIPTION: SEQ ID NO: 12:

Ser Val Arg Val Glu Gln
1               5

(2) INFORMATION FOR SEQ ID NO: 13:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: protein (iii) HYPOTHETICAL: NO (xi) SEQUENCE DESCRIPTION: SEQ ID NO: 13:

Gln Ile Pro Gly Tyr Ile Val Asp Asp Ser Val Arg
1               5                   10

(2) INFORMATION FOR SEQ ID NO: 14:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: protein (iii) HYPOTHETICAL: NO (xi) SEQUENCE DESCRIPTION: SEQ ID NO: 14:

Ile Val Asp Asp
1
```